(12) United States Patent
Dooley et al.

(10) Patent No.: US 6,490,484 B2
(45) Date of Patent: Dec. 3, 2002

(54) APPARATUS AND METHOD FOR ESTIMATING BATTERY CONDITION IN IMPLANTABLE CARDIOVERTER/ DEFIBRILLATORS

(75) Inventors: Michael W. Dooley, St. Paul, MN (US); Gregory Scott Munson, Golden Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 43 days.

(21) Appl. No.: 09/768,929

(22) Filed: Jan. 24, 2001

(65) Prior Publication Data

US 2002/0099416 A1 Jul. 25, 2002

(51) Int. Cl.$^7$ ................................................ A61N 1/39
(52) U.S. Cl. .............................. 607/5; 607/29; 320/136
(58) Field of Search ................... 607/4–8, 29; 320/136

(56) References Cited

U.S. PATENT DOCUMENTS

| 4,290,429 A | 9/1981 | Blaser .................. 128/419 PT |
| 4,313,079 A | 1/1982 | Lee .............................. 320/48 |
| 4,324,251 A | 4/1982 | Mann .................... 128/419 PT |
| 4,448,197 A | 5/1984 | Nappholz et al. ...... 128/419 PT |
| 4,606,350 A | 8/1986 | Frost ..................... 128/419 PG |
| 4,686,990 A | 8/1987 | Moberg ................. 128/419 PT |
| 4,715,381 A | 12/1987 | Moberg ................. 128/419 PT |
| 5,137,020 A | 8/1992 | Wayne et al. .......... 128/419 PS |
| 5,344,431 A | 9/1994 | Merritt et al. ................. 607/29 |
| 5,369,364 A | 11/1994 | Renirie et al. ............... 324/430 |
| 5,370,668 A | 12/1994 | Shelton et al. ................ 607/29 |
| 5,391,193 A | 2/1995 | Thompson ..................... 607/29 |
| 5,458,624 A | 10/1995 | Renirie et al. ................ 607/29 |
| 5,620,474 A | 4/1997 | Koppman ..................... 607/29 |
| 5,800,472 A | 9/1998 | Mann ........................... 607/29 |
| 5,861,006 A * | 1/1999 | Kroll ............................. 607/5 |
| 5,899,923 A * | 5/1999 | Kroll et al. .................... 607/5 |
| 5,904,705 A * | 5/1999 | Kroll et al. .................... 607/5 |
| 5,925,068 A * | 7/1999 | Kroll ............................ 607/29 |
| 6,283,985 B1 * | 9/2001 | Harguth et al. ................ 607/1 |

* cited by examiner

Primary Examiner—Andrew M. Dolinar
(74) Attorney, Agent, or Firm—Schwegman, Lundberg, Woessner & Kluth, P.A.

(57) ABSTRACT

An apparatus and method for determining the condition of a battery in an implantable cardioverter/defibrillator. A battery's operating status is determined from measurements of its open circuit voltage and the time required to charge an energy storage capacitor.

22 Claims, 4 Drawing Sheets

| Open Circuit Voltage Measurement $V_{OC}$ | Open Circuit Voltage Status OCVS |
|---|---|
| $V_{OC} >$ BatteryMOLVoltageLimit | BOL |
| BatteryERIVoltageLimit $<V_{OC} \leq$ BatteryMOLVoltageLimit | MOL |
| BatteryEOLVoltageLimit $<V_{OC} \leq$ BatteryERIVoltageLimit | ERI |
| $V_{OC} \leq$ BatteryEOLVoltageLimit | EOL |

Fig. 3A

| CTM | BOL (ERI_ctr=0) | MOL (ERI_ctr=0) | ERI (ERI_ctr=2) | EOL (ERI_ctr=0) |
|---|---|---|---|---|
| CTM<T$_{3MO}$ | Reset Capform | Set BOL Reset Capform | Dec ERI_ctr Confirm | Dec ERI_ctr Set ERI; confirm |
| T$_{3MO}$ ≤ CTM<T$_{1MO}$ | Inc ERI_ctr Confirm | Reset Capform | Dec ERI_ctr Confirm | Dec ERI_ctr Set ERI; confirm |
| T$_{1MO}$ ≤ CTM<T$_{ERI}$ | Inc ERI_ctr Confirm | Inc ERI_ctr Confirm | No Change | Dec ERI_ctr Set ERI; confirm |
| T$_{ERI}$<CTM<T$_{EOL}$ | Inc ERI_ctr Confirm | Inc ERI_ctr Confirm | No Change | Dec ERI_ctr Set ERI; confirm |
| T$_{EOL}$≤CTM | ERI_ctr=2 Set_EOL | ERI_ctr=2 Set_EOL | ERI_ctr=2 Set_EOL | No Change |

Fig.3B

| CTM | BOL | MOL | ERI | EOL |
|---|---|---|---|---|
| CTM<T3MO | ERI_ctr=0<br>Reset Capform | Set BOL;<br>ERI_ctr=0<br>Reset Capform | Set BOL;<br>ERI_ctr=0<br>Reset Capform | N/A |
| T3MO≤CTM<T1MO | SetMOL;ERI_ctr=0<br>Reset Capform | SetMOL;ERI_ctr=0<br>Reset Capform | SetMOL;ERI_ctr=0<br>Reset Capform | N/A |
| T1MO ≤ CTM<TERI | SetERI;ERI_ctr=2<br>Reset Capform | SetERI;ERI_ctr=2<br>Reset Capform | SetERI;ERI_ctr=2<br>Reset Capform | N/A |
| TERI<CTM<TEOL | SetERI;ERI_ctr=2<br>Reset Capform | SetERI;ERI_ctr=2<br>Reset Capform | SetERI;ERI_ctr=2<br>Reset Capform | N/A |
| TEOL≤CTM | ERI_ctr=2<br>Set_EOL | ERI_ctr=2<br>Set_EOL | ERI_ctr=2<br>Set_EOL | N/A |

Fig. 3C

APPARATUS AND METHOD FOR ESTIMATING BATTERY CONDITION IN IMPLANTABLE CARDIOVERTER/ DEFIBRILLATORS

FIELD OF THE INVENTION

This invention pertains to systems and methods for operating battery-powered implantable medical devices.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. Implantable cardioverter/defibrillators (ICDs) are devices that provide defibrillation therapy by delivering a shock pulse to the heart when a tachyarrhythmia such as fibrillation is detected and typically may also provide pacing therapy. An ICD is an electronic device containing a shock pulse generator that is usually implanted into the chest or abdominal wall. Electrodes connected by leads to the ICD are placed on the heart, or passed transvenously into the heart, to sense cardiac activity and to conduct the impulses from the pulse generator. Typically, the leads have electrically conductive coils along their length that act as electrodes. ICDs can be designed to treat either atrial or ventricular tachyarrhythmias, or both, by delivering a shock pulse that impresses an electric field between the electrodes to which the pulse generator terminals are connected. ICDs typically use an electrolytic capacitor that is charged from a battery with an inductive boost converter to deliver the shock pulse. When ventricular fibrillation is detected, the ICD charges up the capacitor to a predetermined value for delivering a shock pulse of sufficient magnitude to convert the fibrillation (i.e., the defibrillation threshold). The capacitor is then connected to the shock electrodes disposed in the heart to deliver the shock pulse.

ICDs are powered by a battery contained within the housing of the device that has a limited life span. When the battery fails, it must be replaced which necessitates a reimplantation procedure. The useful life of the battery may vary in each individual case and depends upon the specific battery and the power requirements of the device. For example, a device which must deliver paces and/or defibrillation shocks on a frequent basis will shorten the useful life of the battery. As the battery depletes, it is desirable to provide a means of determining that the battery is near the end of its life so that replacement of the battery can be scheduled rather than done on an emergency basis.

SUMMARY OF THE INVENTION

The present invention is a method and apparatus for monitoring the condition of a battery in an implantable medical device such as an implantable cardioverter/ defibrillator. In accordance with the invention, the open circuit voltage of the battery and the time required to charge an electrolytic energy storage capacitor to a specified full voltage value are both measured on an intermittent or periodic basis. The capacitor charge time measurement may be taken during periodic reforming of the electrolytic energy storage capacitor. The operating status of the battery may then be designated as being one of a plurality of battery states ranging from best to worst based upon those measurements. In one embodiment, a similar set of battery states are used to represent the open circuit voltage status and the capacitor charge time status of the battery. The battery operating status is then the worse of the open circuit voltage status and the capacitor charge time status. In order to detect deterioration in the battery's condition in a more timely manner, the time interval for reforming the energy storage capacitor and measuring the capacitor charge time is adjusted based upon the present battery operating status.

BRIEF DESCRIPTION OF THE DRAWINGS

FIGS. 3A through 3C illustrate an exemplary embodiment of the method for monitoring and reporting battery status.

DETAILED DESCRIPTION

Figure 1:
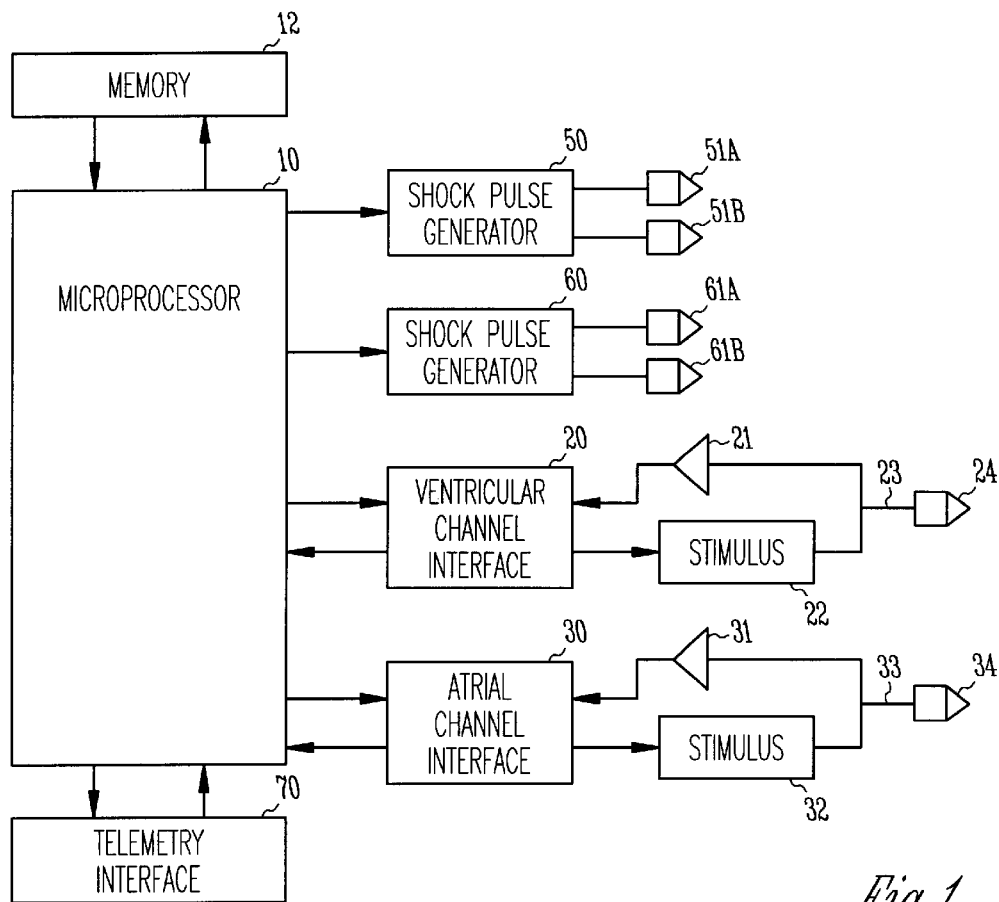
FIG. 1 is a system diagram of an implantable defibrillator.

As a battery in an implantable device progressively depletes, two parameters are affected: the open circuit voltage of the battery decreases and the battery's internal resistance increases. Both of these are useful in determining how near the battery is to the end of its life. Voltage monitoring circuitry may be employed to intermittently measure and record the voltage across the battery's terminals. In order to determine the battery's internal resistance, the time required to charge the defibrillation capacitor may also be measured and recorded. The capacitor charges with a charge time dependent upon the internal resistance of the battery and the capacitance of the capacitor, and the capacitor charge time is thus reflective of changes in the battery's internal resistance.

As noted above, most ICDs today utilize electrolytic capacitors as energy storage devices for delivering defibrillation shocks in order to achieve the necessary energy density. In an aluminum electrolytic capacitor, a thin layer of aluminum oxide is electrolytically formed on the surface of an aluminum anode. The oxide layer then acts as a dielectric when a voltage is applied between a cathode and the aluminum anode, and leakage current is not significant as long as the applied voltage is not greater than the voltage used to form the oxide layer. A problem associated with electrolytic capacitors, however, is deforming of the oxide layer which reduces its thickness and occurs as a result of unavoidable chemical reactions within the capacitor. In order to alleviate this problem in an ICD, the capacitor may be periodically reformed by charging it to a specified full voltage for a specified period of time, and then either discharging it through an internal load or leaving it in a charged state to leak off naturally. The capacitor charge time may thus also be measured during a capacitor reforming procedure and used to determine the battery's operating status.

In accordance with the present invention, the operating status of a battery in an implantable cardioverter/defibrillator is determined from measurements of the battery's open circuit voltage and the time required to charge an electrolytic capacitor during a reforming procedure. The open circuit battery voltage is periodically or intermittently measured, and a present open circuit voltage status is determined as being one of a plurality of open circuit voltage status states ranging from best to worst based upon the voltage measurement. Similarly, the time required for charging the electrolytic capacitor during periodic or intermittent reforming is measured, and a present capacitor charge time status is determined as being one of a plurality of capacitor charge time states ranging from best to worst based upon the charge time measurement. The present operating status of the battery is then determined to be one of a plurality of operating status states ranging from best to worst based upon a combination of the present open circuit voltage status and capacitor charge time status. In one embodiment, the present battery operating status is selected as the worse of the present capacitor charge time status and the present open circuit voltage status.

In order to detect a deterioration in the battery's condition in a more timely manner, the time interval for periodically reforming the electrolytic capacitor is adjusted as a function of the present operating status of the battery. This allows any further deterioration in the battery's condition to be detected earlier than would otherwise be the case. For example, the battery operating status states include a beginning-of-life state, a mid-life state, and an end-of-life state, and the capacitor reforming interval is shortened when the present battery operating status reaches a specified state worse than the beginning-of-life state. In a more particular embodiment, the battery operating status states include a beginning-of-life state, a mid-life state, an elective-replacement-interval state, and an end-of-life state. The capacitor reforming interval is changed from an initially specified first value to a specified shorter second value when the present battery operating status reaches a specified state worse than the beginning-of-life state. For example, the capacitor may initially be reformed at three month intervals. When the battery's condition deteriorates, as indicated by a progression from the beginning-of-life state to, for example, the middle-of-life state, the reforming interval is changed to one month.

In a further refinement to the method, confirmation measurements may be required before a status relating to the battery is changed. For example, the capacitor charge time status may only be changed when a first charge time measurement indicates a change in capacitor charge time status and a second confirmation charge time measurement occurring within a specified time interval after the first charge time measurement also indicates a change in capacitor charge time status. Similarly, a confirmation open circuit voltage measurement may be required to occur within a specified time after a first measurement before the present open circuit voltage status is changed. In certain embodiments, a change to end-of-life status may still be allowed occur after only one capacitor charge time or open circuit voltage measurement without the need of a confirmation measurement. It may also be desirable to latch the end-of-life state such that once a status reaches the end-of-life state, no further improvements in the status are permitted.

In order for capacitor charge time measurements to be uniform, it is preferable to for such measurements to be performed during only those capacitor reforming procedures in which a full-energy capacitor charge has taken place. A full-energy charge is one in which the capacitor is charged to specified full voltage value starting from a voltage which is no greater than a specified percentage of the full voltage value. For example, a specified percentage of the full voltage value may be set so that only those reforming procedures in which the capacitor is charged to a full value from an initial voltage that is 5% of the full value are used to determine the charge time status of the battery. Also, with certain types of capacitors, it may be possible to take capacitor charge time measurements when the capacitor is charged to deliver a defibrillation shock rather than only during reforming procedures if the full-energy charge requirements are met.

FIG. 1 is a system diagram of a microprocessor-based implantable cardioverter/defibrillator device for treating atrial and/or ventricular tachyarrhythmias that also incorporates a pacemaker functionality. The device is powered by a battery contained within the device housing. In this embodiment, a microprocessor and associated circuitry make up the controller of the device, enabling it to output pacing or shock pulses in response to sensed events and lapsed time intervals. The microprocessor 10 communicates with a memory 12 via a bidirectional data bus. The memory 12 typically comprises a ROM or RAM for program storage and a RAM for data storage. The controller may be configured with appropriate firmware to determine the operating status of the battery by the method described herein. A telemetry interface 70 is provided for enabling communication with an external programmer so that various operating parameters may be reported, including the operating status of the battery, as well as allowing reprogramming of the device.

The ICD has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The sensing channels are used to control pacing and for measuring heart rate in order to detect tachyarrhythmias such as fibrillation. The ICD detects. an ventricular tachyarrhythmia, for example, by measuring the ventricular rate as well as possibly performing other processing on data received from ventricular sensing channel. A shock pulse generator 50 is interfaced to the microprocessor for delivering shock pulses to the ventricles via a pair of terminals 51a and 51b that are connected by defibrillation leads to shock electrodes placed in proximity to the ventricles. A similar shock pulse generator 60 and shock electrodes 61a and 61b are provided to deliver atrial defibrillation therapy.

Figure 2:
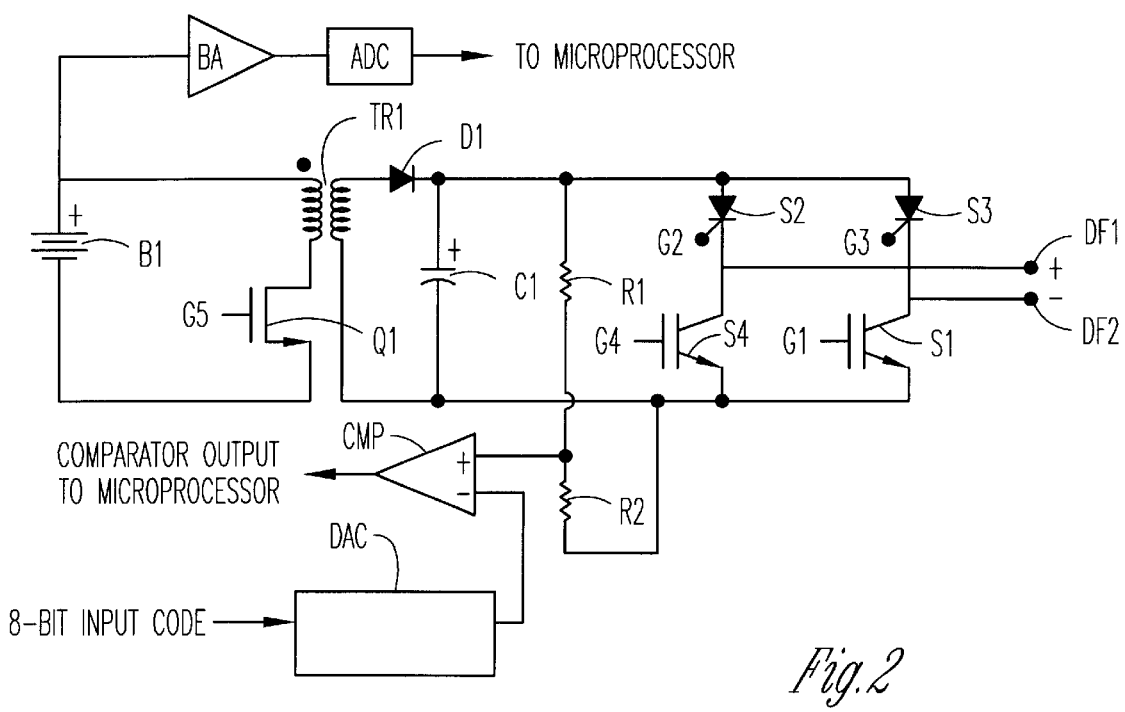
FIG. 2 is a diagram of the capacitor charging circuit.

FIG. 2 shows the components of the shock pulse generator and capacitor charging circuitry in more detail. The shock electrodes are connected to defibrillation terminals DF1 and DF2 which are switchably connected to an energy storage capacitor C1 by switches S1 through S4 in a so-called H-configuration. When a shock pulse is delivered, the defibrillation terminals are connected by the aforementioned switches to the capacitor. C1 to thereby impress the capacitor voltage across the shock electrodes. Switches S1 through S4 are solid-state device having gate voltages G1 through G4, respectively, that are controlled by the microprocessor 10. By controlling the gate voltages of the switches, the microprocessor can control the polarity of the shock pulse delivered to the electrodes as well as deliver monophasic or biphasic shock waveforms.

The capacitor C1 is charged from battery B1 to a specified voltage by a charging circuit before each defibrillation shock and during a capacitor reforming procedure. The charging circuit in this embodiment is a boost converter which includes a transformer TR1 and a transistor switch Q1. Transistor Q1 is an FET having its gate voltage G5 connected to the output of an oscillator and includes circuitry for monitoring the drain current to avoid saturating the transformer core. The oscillator (not shown) outputs pulses to switch current on and off in the primary coil of the transformer TR1 and is controlled by the microprocessor 10. The width and/or frequency of the oscillator pulse output may also be controlled in accordance with the primary coil current sensed by transistor Q1. The coils of the transformer TR1 are coupled inductors that receive current from battery B1 during short intervals as dictated by the state of transistor Q1. When transistor Q1 is switched off, the energy stored in the inductance of the transformer is transferred to the capacitor C1 through a diode D1. The capacitor voltage is monitored by circuitry that includes a voltage divider, made up of resistors R1 and R2, and a comparator CMP. The voltage divider feeds the capacitor voltage to the comparator CMP where it is compared with a reference voltage specified by the microprocessor through digital-to-analog converter DAC. The comparator output is then input to the microprocessor which controls the operation of the boost converter to charge the capacitor voltage to a specified level. The microprocessor determines the capacitor charge time by measuring the time from the beginning of the charging cycle until the output of the comparator indicates that the capacitor has been charged to the reference voltage. A buffer amplifier BA and analog-to-digital converter ADC are also provided which feeds the battery voltage to the microprocessor for measuring the open circuit battery voltage when no loads are connected.

FIGS. 3A through 3C illustrate a specific embodiment of the invention as described above in general terms. In this embodiment, four states are used to indicate the open circuit voltage status (OCVS) and the capacitor charge time status (CCTS) starting from best to worst: beginning-of-life (BOL), middle-of-life (MOL), elective replacement interval (ERI), and end-of-life (EOL). The battery operating status is then determined as the worse of the OCVS and the CCTS.

FIG. 3A is a table showing how open circuit voltage measurements are used to determine the OCVS. The open circuit voltage measurement $V_{oc}$ is compared with three limit values to determine the OCVS: BatteryMOLVoltageLimit, BatteryERIVoltageLimit, and BatteryEOLVoltageLimit. The results of the comparison then map the OCVS to either the BOL, MOL, ERI, or EOL states as shown in the figure.

FIGS. 3B and 3C show how capacitor charge time measurements during capacitor reforming are used to determine the capacitor charge time status. In this embodiment, the reforming interval is initially set to be three months. The charge time measurement CTM is compared with three limit values to determine the CCTS: $T_{1MO}$, $T_{3Mo}$, $T_{ERI}$, and $T_{EOL}$. As shown in FIG. 3B, the results of the comparison dictate that either no change is made to the CCTS or that a confirmation measurement should scheduled to occur a specified interval (e.g., 24 hours from the time of the first measurement). The notation "Reset Capform" refers to resetting of the capacitor reforming interval such that the interval for periodically reforming the capacitor is restarted. In all cases, the specified action is taken only if a full-energy capacitor charge has occurred. A counter ERI_ctr which ranges from a value of 0 to 2 is either incremented or decremented to serve as a flag indicating whether a measurement is a first measurement or a confirmation measurement. FIG. 3C shows how the charge time measurements are then used to update the CCTS. After each updating of the CCTS, either during a first measurement or a confirmation measurement, the capacitor reforming interval is reset. In order to detect deterioration in the battery's condition, the capacitor reforming interval is adjusted in accordance with the present battery operating status. For example, the reforming interval may be adjusted from three months to one month when the battery operating status reaches the MOL state.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for determining the operating status of a battery in an implantable cardioverter/defibrillator, comprising:

intermittently measuring an open circuit battery voltage, and determining a present open circuit voltage status as being one of a plurality of open circuit voltage status states ranging from best to worst based upon the voltage measurement;

intermittently reforming an electrolytic capacitor by charging the capacitor to full voltage and measuring the time required for such charging, and determining a present capacitor charge time status as being one of a plurality of capacitor charge time states ranging from best to worst based upon the charge time measurement;

determining a present operating status of the battery to be one of a plurality of operating status states ranging from best to worst based upon a combination of the present open circuit voltage status and capacitor charge time status; and, adjusting a time interval for periodically reforming the electrolytic capacitor in a manner dependent upon the present operating status of the battery.

2. The method of claim 1 wherein the battery operating status states include a beginning-of-life state, a mid-life state, and an end-of-life state, and wherein the capacitor reforming interval is shortened when the present battery operating status reaches a specified state worse than the beginning-of-life state.

3. The method of claim 2 wherein the battery operating status states include a beginning-of-life state, a mid-life state, an elective-replacement-interval state, and an end-of-life state, and wherein the capacitor reforming interval is changed from an initially specified first value to a specified shorter second value when the present battery operating status reaches a specified state worse than the beginning-of-life state.

4. The method of claim 2 wherein the capacitor reforming interval is initially specified with a first value of three months when the battery operating status is in the beginning-of-life state and is changed to a second value of one month when the present battery operating status reaches a specified state worse than the beginning-of-life state.

5. The method of claim 4 wherein the specified state worse than the beginning-of-life state when the capacitor reforming interval is changed to one month is the middle-of-life state.

6. The method of claim 1 wherein the capacitor charge time states and the open circuit voltage states each include a beginning-of-life state, a mid-life state, and an end-of-life state, and wherein the present battery operating status is selected as the worse of the present capacitor charge time status and the present open circuit voltage status.

7. The method of claim 1 wherein the capacitor charge time status is only changed when a first charge time measurement indicates a change in capacitor charge time status and a second confirmation charge time measurement occurring within a specified time interval after the first charge time measurement also indicates a change in capacitor charge time status.

8. The method of claim 7 wherein a change to end-of-life status may occur after only one capacitor charge time measurement indicative of such with no confirmation needed.

9. The method of claim 1 wherein the capacitor charge time status can only be changed by a capacitor charge time measurement in which the capacitor is charged to specified full voltage value starting from a voltage which is no greater than a specified percentage of the full voltage value.

10. The method of claim 1 wherein the specified percentage of the full voltage value is 5%.

11. The method of claim 9 wherein the capacitor charge time status may be changed by a capacitor charge time measurement taken when the capacitor is charged to deliver a defibrillation shock.

12. The method of claim 1 wherein the open circuit voltage status is only changed when a first voltage measurement indicates a change in open circuit voltage status and a second confirmation voltage measurement occurring within a specified time interval after the first voltage measurement also indicates a change in open circuit voltage status.

13. The method of claim 2 wherein the battery operating status is unaffected by subsequent measurements once it reaches the end-of-life state.

14. An implantable cardioverter/defibrillator device, comprising:

a sensing channel for sensing cardiac depolarizations;

an energy storage capacitor switchably connected to shock electrodes for delivering a defibrillation shock pulse;

a battery;

a charging circuit for charging the energy storage capacitor from the battery;

a voltage monitor for monitoring the voltage of the energy storage capacitor;

a controller for operating the charging circuit to charge the energy storage capacitor to a specified voltage upon detection of an arrhythmia and delivering a defibrillation shock pulse by switching the energy storage capacitor to the shock electrodes; and, wherein the controller is configured to:

intermittently measure an open circuit battery voltage, and determine a present open circuit voltage status as being one of a plurality of open circuit voltage status states ranging from best to worst based upon the voltage measurement;

intermittently reform the energy storage capacitor by charging the capacitor to full voltage and measure the time required for such charging, and determine a present capacitor charge time status as being one of a plurality of capacitor charge time states ranging from best to worst based upon the charge time measurement;

determine a present operating status of the battery to be one of a plurality of operating status states ranging from best to worst based upon a combination of the present open circuit voltage status and capacitor charge time status; and, adjust a time interval for periodically reforming the electrolytic capacitor in a manner dependent upon the present operating status of the battery.

15. The device of claim 14 wherein the battery operating status states include a beginning-of-life state, a mid-life state, and an end-of-life state, and wherein the capacitor reforming interval is shortened when the present battery operating status reaches a specified state worse than the beginning-of-life state.

16. The device of claim 15 wherein the battery operating status states include a beginning-of-life state, a mid-life state, an elective-replacement-interval state, and an end-of-life state, and wherein the capacitor reforming interval is changed from an initially specified first value to a specified shorter second value when the present battery operating status reaches a specified state worse than the beginning-of-life state.

17. The device of claim 16 wherein the capacitor reforming interval is initially specified with a first value of one month when the battery operating status is in the beginning-of-life state and is changed to a second value of three months when the present battery operating status reaches a specified state worse than the beginning-of-life state.

18. The device of claim 17 wherein the specified state worse than the beginning-of-life state when the capacitor reforming interval is changed to three months is the middle-of-life state.

19. The device of claim 14 wherein the capacitor charge time states and the open circuit voltage states each include a beginning-of-life state, a mid-life state, and an end-of-life state, and wherein the present battery operating status is selected as the worse of the present capacitor charge time status and the present open circuit voltage status.

20. The device of claim 14 wherein the capacitor charge time status is only changed when a first charge time measurement indicates a change in capacitor charge time status and a second confirmation charge time measurement occurring within a specified time interval after the first charge time measurement also indicates a change in capacitor charge time status.

21. The device of claim 20 wherein a change to end-of-life status may occur after only one capacitor charge time measurement indicative of such with no confirmation needed.

22. The device of claim 14 wherein the capacitor charge time status can only be changed by a capacitor charge time measurement in which the capacitor is charged to specified full voltage value starting from a voltage which is no greater than a specified percentage of the full voltage value.

* * * * *

UNITED STATES PATENT AND TRADEMARK OFFICE
CERTIFICATE OF CORRECTION

| | |
|---|---|
| PATENT NO. | : 6,490,484 B2 |
| DATED | : December 3, 2002 |
| INVENTOR(S) | : Michael W. Dooley and Gregory S. Munson |

It is certified that error appears in the above-identified patent and that said Letters Patent is hereby corrected as shown below:

<u>Column 7,</u>
Line 4, delete "claim 1" and insert -- claim 9 -- therefor.

Signed and Sealed this

Nineteenth Day of August, 2003

JAMES E. ROGAN
*Director of the United States Patent and Trademark Office*